United States Patent [19]

Hagen et al.

[11] 4,206,217
[45] Jun. 3, 1980

[54] 3-[4-(1,3-DIAZACYCLOALKEN-2-YL)-PHENYL]-1,2-BENZISOTHIAZOLES, THEIR MANUFACTURE, AND DRUGS CONTAINING THESE COMPOUNDS

[75] Inventors: Helmut Hagen, Frankenthal; Dieter Lenke, Ludwigshafen; Gerda von Philipsborn, Weinheim, all of Fed. Rep. of Germany

[73] Assignee: BASF Aktiengesellschaft, Fed. Rep. of Germany

[21] Appl. No.: 928,815

[22] Filed: Jul. 28, 1978

[30] Foreign Application Priority Data

Aug. 3, 1977 [DE] Fed. Rep. of Germany ....... 2734882

[51] Int. Cl.$^2$ ............................................. C07D 277/62
[52] U.S. Cl. .................................... 424/270; 544/333; 548/336; 548/207
[58] Field of Search ................... 260/304 A; 424/270; 544/333; 548/336

[56] References Cited

U.S. PATENT DOCUMENTS

| | | | |
|---|---|---|---|
| 3,549,624 | 12/1970 | Conover et al. | 544/333 |
| 3,557,115 | 1/1971 | Manning | 544/333 |
| 4,147,698 | 4/1979 | Wade et al. | 424/270 |
| 4,148,798 | 4/1979 | Wade et al. | 424/270 |

OTHER PUBLICATIONS

Chemical Abstracts, vol. 58, 11340c (1963).
Chemical Abstracts, vol. 59, 8721e (1963).

Primary Examiner—Nicholas S. Rizzo
Attorney, Agent, or Firm—Keil & Witherspoon

[57] ABSTRACT

3-[4-(1,3-Diazacyclo-2-yl)]-1,2-benzisothiazoles, their addition salts with acids, their manufacture, and pharmaceutical formulations which contain these compounds as active ingredients and which may be used for the pharmacotherapy of cardiac arrhythmias.

7 Claims, No Drawings

3-[4-(1,3-DIAZACYCLOALKEN-2-YL)-PHENYL]-1,2-BENZISOTHIAZOLES, THEIR MANUFACTURE, AND DRUGS CONTAINING THESE COMPOUNDS

The present invention relates to novel 3-[4-(1,3-diazacycloalken-2-yl)-phenyl]-1,2-benzisothiazoles and to their addition salts with acids, their manufacture, and pharmaceutical formulations containing these compounds.

We have found that compounds of the general formula I

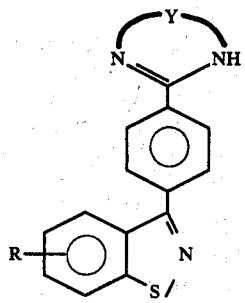

where R is hydrogen, alkyl of 1 to 4 carbon atoms, alkoxy of 1 to 3 carbon atoms, halogen or nitro and Y is a bridge member of the formula

—CH₂—CH₂—,

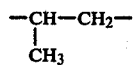

or

—CH₂—CH₂—CH₂, and their physiologically acceptable addition salts with acids, exhibit valuable pharmacological properties.

Preferably, amongst the above meanings, R is hydrogen, halogen, especially chlorine or bromine, or nitro, and Y is 1-methyl-1,2-ethylene or 1,3-trimethylene.

In particularly preferred compounds, R is hydrogen and Y is

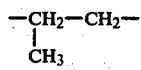

or

—CH₂—CH₂—CH₂—.

Accordingly, examples to be mentioned of the compounds of the invention, which can be collectively described as 3-[4-(1,3-diazacyclo-2-yl)]-1,2-benzisothiazoles, are: 3-[4-imidazolin-2-yl)-phenyl]-1,2-benzisothiazole, 3-[4-(methylimidazolin-2-yl)-phenyl]-1,2-benzisothiazole, 3-[4-(tetrahydropyrimidin-2-yl)-phenyl]-1,2-benzisothiazole, 5-chloro-3-[4-(imidazolin-2-yl)-phenyl]-1,2-benzisothiazole, 5-chloro-3-[4-(methylimidazolin-2-yl)-phenyl]-1,2-benzisothiazole, 4-methoxy-3-[(4-methylimidazolin-2-yl)-phenyl]-1,2-benzisothiazole, 5-nitro-3-[4-(imidazolin-2-yl)-phenyl]-1,2-benzisothiazole, 5-nitro-3-[4-(tetrahydropyrimidin-2-yl)-phenyl]-1,2-benzisothiazole and 5-bromo-6-chloro-3-[4-(imidazolin-2-yl)-phenyl]-1,2-benzisothiazole.

The compounds according to the invention may be manufactured by reacting a compound of the general formula II

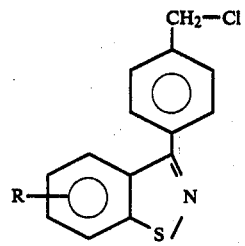

where R has the above meanings, with a diamine of the general formula III

H₂N—Y—NH₂    (III)

where Y has the above meanings, and elementary sulfur, advantageously in an inert organic solvent, after which the resulting compound may or may not be converted into a physiologically acceptable addition salt with an acid.

The reaction is advantageously carried out at from 40° to 150° C., preferably at from 70° to 120° C.

Suitable solvents for the reaction are aromatic hydrocarbons, especially benzene hydrocarbons, eg. benzene and toluene, lower alcohols, eg. methanol, ethanol, propanol, isopropanol, butanol and isobutanol, saturated cyclic and aliphatic ethers, eg. dibutyl ether and dioxane, glycol ethers, especially monoalkyl ethers of glycol, eg. glycol monomethyl ether and glycol monoethyl ether, and mixtures of the above solvents.

Amongst the above solvents, the benzene hydrocarbons, especially benzene and toluene, and the monoalkyl ethers of glycol, especially glycol monomethyl ether, are preferred.

The diamine of the formula III is used in the stoichiometric amount or in excess, where appropriate in up to 3 times the stoichiometric amount, based on the compound of the formula II.

The elementary sulfur is used in stoichiometric amount or in excess, viz. up to a 1,2-fold excess over the stoichiometric amount, based on the chloromethyl compound used. Preferably, the stoichiometric amount of elementary sulfur is used.

By way of example, the reaction of 3-(4-chloromethylphenyl)-1,2-benzisothiazole with ethylenediamine and sulfur may be represented by the following equation:

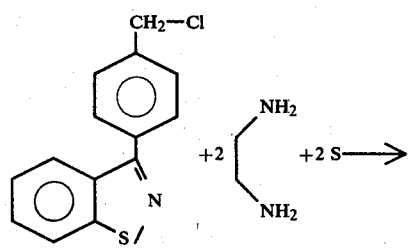

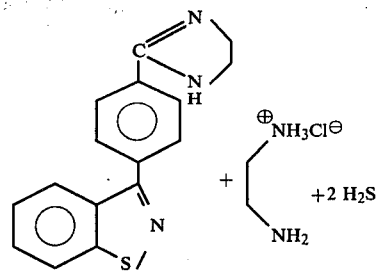

The starting compounds of the formula II may be obtained, for example, by side-chain chlorination of 3-(4-methylphenyl)-1,2-benzisothiazoles with chlorine at about 170° C. under UV irradiation.

The 3-(4-methylphenyl)-1,2-benzisothiazoles on which the compounds of the formula II are based may be obtained by reacting an o-haloarylketone of the formula

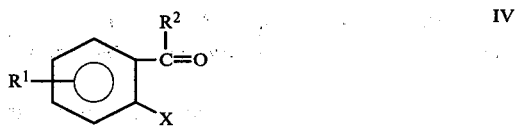

IV where $R^1$ has the meanings given for R in formula I, $R^2$ is 4-methylphenyl and X is halogen, especially chlorine, with ammonia and elementary sulfur in accordance with the principle of the process of German Laid-Open Application 25 03 699.9.

This application discloses as intermediates, compounds where $R^2$ is hydrogen, ie. aldehydes, instead of compounds of the formula IV, ie. ketones. The reaction of a ketone of the formula IV, is illustrated below, in Example A.1. A corresponding patent application was filed in the Federal Republic of Germany on 3rd Aug. 1977 under file reference P 27 34 866.9. A corresponding patent application, claiming the said German priority, was also filed in the United States as Ser. No. 926,446, filed July 26, 1978.

The starting material IV, ammonia and elementary sulfur are used in about stoichiometric amounts, but a ratio of from 2 to 10 moles of ammonia and from 0.9 to 1.1 gram atom of sulfur per mole of starting material IV is preferred.

This reaction is as a rule carried out at from 20 to 250° C., advantageously from 20° to 200° C., preferably from 40° to 180° C., and especially from 40° to 130° C., under atmospheric or superatmospheric pressure, continuously or batchwise. The reaction pressure is in general determined by the total vapor pressure of the components at the reaction temperature. Organic solvents which are inert under the reaction conditions may or may not be used, examples of such solvents being aromatic hydrocarbons, eg. toluene, ethylbenzene, o-, m- and p-xylene and isopropylbenzene; alkanols and cycloalkanols, eg. ethanol, n-butanol, isobutanol, methylglycol, cyclohexanol, propanol, methanol and 2-ethylhexanol; ethers, eg. ethyl propyl ether, diisobutyl ether, methyl tert.-butyl ether, n-butyl ethyl ether, di-n-butyl ether, dioxane, diisoamyl ether, diisopropyl ether, anisole, phenetole, cyclohexyl methyl ether, diethyl ether, tetrahydrofuran and thioanisole, and mixtures of the above. The solvent is advantageously used in an amount of from 200 to 10,000 percent by weight, preferably from 300 to 1,000 percent by weight, based on starting material IV.

The reaction may be carried out as follows: the starting material IV, elementary sulfur and ammonia are reacted, in the presence or absence of a solvent, for from 3 to 10 hours at the above temperature in a pressure reactor. The 1,2-benzisothiazole is obtained from the reaction mixture by conventional methods, for example by fractional distillation and filtration, with or without subsequent recrystallization from a suitable solvent, eg. light naphtha. It is also possible to remove excess ammonia and solvent, then pour the reaction mixture into water, extract the resulting mixture with a suitable solvent, eg. methylene chloride or benzene and work up the extract in the above manner.

The novel compounds of the general formula I may or may not be converted, in the conventional manner, to an addition salt with a physiologically acceptable acid. Examples of suitable conventional physiologically acceptable organic or inorganic acids are hydrochloric acid, hydrobromic acid, phosphoric acid and sulfuric acid amongst inorganic acids and oxalic acid, maleic acid, fumaric acid, lactic acid, tartaric acid, malic acid, citric acid, salicylic acid, adipic acid and benzoic acid, amongst organic acids; examples of acids may also be found in Fortschritte der Arzneimittelforschung, volume 10, pages 224–225, Birkhäuser Verlag, Basel and Stuttgart, 1966.

The compounds according to the invention and their physiologically acceptable addition salts with acids are distinguished by a powerful antiarrhythmic effect and are in particular suitable for the pharmacotherapy of cardiac arrhythmias.

The antiarrhythmic activity of the compounds was determined by orally administering these to rats (Sprague Dawley, weight: 180–240 g) 45 minutes before the start of narcosis (100 mg/kg of thiobutabarbital, administered intraperitoneally).

The arrhythmogenous substance used was aconitine, administered by intravenous infusion (at the rate of 0.005 mg/kg.minute) 60 minutes after administration of the compound of the invention. In untreated animals (N=30) arrhythmias manifest themselves after an average of 3.7±0.9 minutes; their occurrence can be delayed by antiarrhythmic agents, the delay being dependent on the dosage.

For a quantitative evaluation of the linear relation between the logarithm of the dose (mg/kg) of the test substances and the relative increase in the duration of infusion of aconitine (Δ%), the dose which increases the duration of infusion by 50% (ED 50%) was determined. The conventional antiarrhythmic agent procainamide was used for comparison.

The acute toxicity was determined on groups of 10 or 20 female Swiss mice weighing 20–26 g, using intraperitoneal administration. The LD 50 was calculated (Probit analysis) as the dose following which 50% of the animals died within 7 days.

Table 1 shows that the antiarrhythmic activity of the compounds of Examples 2 and 3 is about 5 times greater than that of the antiarrhythmic agent procainamide. A further advantage of the novel compounds is that the effect at the maximum dose is 114% (Example 2) or 73% (Example 3) higher than that of procainamide, ie. the aconitine-antagonism of the tested compounds is substantially more pronounced than that of procainamide.

The therapeutic range expressed as the quotient of the lethal dose (LD 50) and the antiarrhythmically active dose (ED 50%) is 4 times greater (Example 2) or 2.8 times greater (Example 3) than for procainamide.

Table 1

| | Antiarrhythmic effect and acute toxicity | | | | | |
|---|---|---|---|---|---|---|
| | Antiarrhythmic effect[1] | | | | Acute toxicity | |
| | Effective dose | | Maximum effect[4] | | | LD 50 | Therapeutic |
| Compound | D 50%[2] | R.E.[3] | Dose | Δ%[5] | R.M.E.[6] | mg/kg | range[7] |
| Example 2 | 31.2 | 5.03 | 215 | 289 | 2.14 | 126 | 4.03 |
| Example 3 | 32.7 | 4.80 | 215 | 233 | 1.73 | 90.5 | 2.76 |
| Procainamide | 157 | 1.00 | 681 | 135 | 1.00 | 227 | 1.00 |

[1] Aconitine-induced arrhythmia in rats
[2] Orally administered dose (mg/kg) which increases the duration of aconitine infusion (min) by 50%
[3] R.E. = relative effect; procainamide = 1.00
[4] Effect of the maximum non-toxic dose
[5] Increase in duration of aconitine infusion, Δ%
[6] R.M.E. = relative maximum effectiveness
[7] $\frac{LD\ 50}{ED\ 50\%}$ In test models used in respect of the antiarrhythmic effect, the following findings were obtained:
Stimulation time/tension relationship (isolated auricle):
Example 2 (tetrahydropyrimidine derivative): 1.24 times the effect of quinidine
Example 3 (methylimidazoline derivative): 1.5 times the effect of quinidine.
Ventricular fibrillation threshold in guinea pigs:
Example 2: intravenous administration, 1.8 times the effect of quinidine
Maximal following frequency in non-narcotized rabbits:
Example 20: intravenous administration, 7 times the effect of quinidine.

Accordingly, the present invention also relates to therapeutic agents or formulations which in addition to conventional excipients and diluents contain a compound of the formula I, or its physiologically acceptable addition salt with an acid, as the active ingredient, and to the use of the novel compounds for therapeutic purposes.

The therapeutic agents or formulations are prepared in the conventional manner by compounding an appropriate dose with the conventional excipients or diluents and the conventional pharmaceutical auxiliaries, in accordance with the desired route of administration.

The preferred formulations are those suitable for oral administration. Examples of these are tablets, film tablets, dragees, capsules, pills, powders, solutions and suspensions, and forms which exert a depot effect.

Of course, formulations for parenteral administration, eg. injection solutions or additives for infusion solutions, may also be used. Suppositories are a further example of suitable formulations.

Appropriate tablets can be obtained, for example, by mixing the active ingredient with conventional auxiliaries, for example inert diluents, eg. dextrose, sugar, sorbitol, mannitol, polyvinylpyrrolidone, calcium carbonate, calcium phosphate or lactose, disintegrating agents, eg. corn starch, alginic acid or polyvinylpyrrolidone, binders, eg. starch or gelatin, lubricants, eg. magnesium stearate or talc and/or agents added in order to achieve a depot effect, eg. carboxypolymethylene, carboxymethylcellulose, cellulose acetate phthalate or polyvinyl acetate. The tablets may also consist of several layers.

Similarly, dragees can be prepared by coating cores, prepared similarly to the above tablets, with conventional dragee-coating agents, eg. collidone or shellac, gum arabic, talc, titanium dioxide or sugar. The dragee coating may also consist of several layers, and the auxiliaries mentioned above, in connection with tablets, may be used.

Solutions or suspensions containing the active ingredients according to the invention may in addition contain flavor improvers, eg. saccharin, cyclamate or sugar, as well as flavorings, e.g. vanillin or orange extract. In addition, they may contain suspension assistants, eg. sodium carboxymethylcellulose, or preservatives, eg. parahydroxybenzoates. Capsules containing active ingredients may be prepared, for example, by mixing the active ingredient with an inert carrier, eg. lactose or sorbitol, and encapsulating the mixture in gelatin capsules.

Suitable suppositories may be prepared, for example, by mixing (the active ingredient) with an appropriate excipient, eg. a neutral fat or a polyethylene glycol or a derivative thereof.

For use in man, a single dose of the compound according to the invention is from 5 to 100 mg, preferably from 10 to 80 mg.

The Examples which follow illustrate the present invention.

A. EXAMPLES OF THE MANUFACTURE OF STARTING COMPOUNDS

EXAMPLE 1

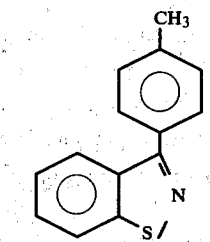

230.5 parts of 2-chloro-4'-methylbenzophenone, 32 parts of sulfur and 100 parts of NH₃ in 800 parts of methylglycol are reacted for 6 hours at 160° C. in an enamelled autoclave. 200 parts of 3-(4'-methylphenyl)-1,2-benzisothiazole, of melting point 56° C., are obtained. The yield corresponds to 89% of theory.

Similarly, 2,5-dichloro-4'-methylbenzophenone, when reacted in the same molar ratio and under the same conditions, with sulfur and ammonia, gives 5- chloro-3-(4'-methylphenyl)-1,2-benzisothiazole, of melting point 121° C., in 85% yield.

2-Chloro-5-nitro-4-methylbenzophenone gives 5-nitro-3-(4'-methylphenyl)-1,2-benzisothiazole, of melting point 179° C., in 90% yield.

EXAMPLE 2

3-(4'-Chloromethylphenyl)-1,2-benzisothiazole 225 g of 3-(4'-methylphenyl)-1,2-benzisothiazole are heated to 170° C. in a stirred apparatus and 100 g of chlorine are passed in over 2 hours whilst irradiating the mixture with a UV lamp. The end point of the reaction is determined by gas chromatography (disappearance of the starting material). The reaction mixture is then cooled and the product is filtered off and recrystallized from methanol. 208 g of 3-(4-chloromethylphenyl)-1,2-benzisothiazole, melting at 86°–89° C., are obtained; this yield corresponds to 80% of theory.

Similarly, 5-chloro-3-(4'-chloromethylphenyl)-1,2-benzisothiazole, of melting point 116° C., is prepared in 78% yield.

B. COMPOUNDS ACCORDING TO THE INVENTION

EXAMPLE 1

3-[4-Imidazolin-2-yl-phenyl]-1,2-benzisothiazole

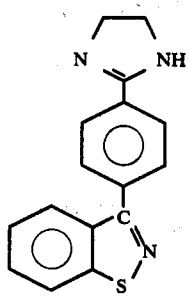

26 g of 3-(4-chloromethylphenyl)-1,2-benzisothiazole, 6.4 g of sulfur and 300 ml of toluene are heated to 50° C. and 12 g of ethylenediamine are added slowly at this temperature. The reaction mixture is then stirred for 15 hours under reflux and is filtered hot, and the filtrate is cooled to 10°–15° C. 21 g of 3-(4-imidazolin-2-yl-phenyl)-1,2-benzisothiazole, melting at 177° C., are obtained. This corresponds to a yield of 75% of theory.

| | | C | H | N | S |
|---|---|---|---|---|---|
| Analysis: | calculated | 68.8 | 4.6 | 15.1 | 11.5 |
| | found | 68.4 | 4.7 | 15.0 | 11.7 |

The hydrochloride of the compound melts at 318° C.

EXAMPLE 2

3-[4-(Tetrahydropyrimidin-2-yl)-phenyl]-1,2-benzisothiazole hydrochloride

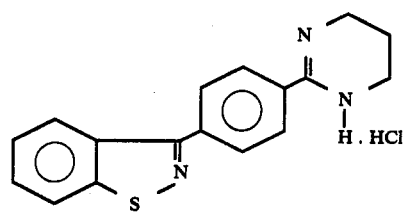

26 g of 3-(4-chloromethylphenyl)-1,2-benzisothiazole, 6.4 g of sulfur and 300 ml of toluene are heated to 50° C. 15 g of 1,3-diaminopropane are added slowly at the same temperature. The reaction mixture is then stirred for 20 hours under reflux. 20 g of hydrogen chloride gas are then passed in over one hour, the mixture is cooled to room temperature and the resulting solid is filtered off. After recrystallization from water in the presence of active charcoal, 18 g of 3-[4-tetrahydropyrimidin-2-yl)-phenyl]-1,2-benzisothiazole hydrochloride, melting, with decomposition, at 314° C., are obtained. The yield corresponds to 54.6% of theory.

| | | C | H | N | S | Cl |
|---|---|---|---|---|---|---|
| Analysis: | calculated | 61.9 | 4.9 | 12.7 | 9.7 | 10.8 |
| | found | 61.4 | 5.1 | 12.4 | 9.9 | 10.9 |

EXAMPLE 3

3-[4-(Methylimidazolin-2-yl)-phenyl]-1,2-benzisothiazole hydrochloride

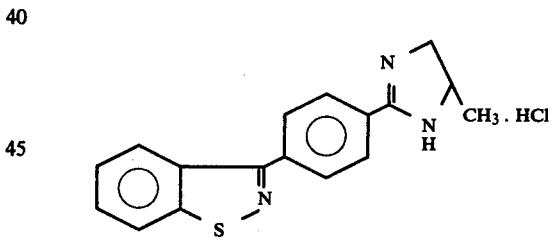

26 g of 3-(4'-chloromethylphenyl)-1,2-benzisothiazole, 6.4 g of sulfur and 15 g of 1,2-diaminopropane in 400 ml of glycol monomethyl ether are heated for 15 hours at 110° C. After distilling off the solvent, the residue is dissolved in 50 g of methanol and this solution is stirred into 400 g of ethereal hydrochloric acid (15 g of HCl in diethyl ether), whilst cooling. The crystals formed are filtered off and dissolved in 300 parts of water, the solution is filtered and the filtrate is rendered alkaline with concentrated NaOH and extracted with methylene chloride. The methylene chloride phase is dried and 20 g of hydrogen chloride gas are passed in. 17 g of the desired end product are obtained as colorless crystals, melting at 243° C. The yield corresponds to 52% of theory.

| | | C | H | N | S | Cl |
|---|---|---|---|---|---|---|
| Analysis: | calculated | 61.9 | 4.9 | 12.7 | 9.7 | 10.8 |

| -continued | | | | | |
|---|---|---|---|---|---|
| | C | H | N | S | Cl |
| found | 61.8 | 5.0 | 12.6 | 9.7 | 10.8 |

EXAMPLE 4

5-Chloro-3-[4-(imidazolin-2-yl)-phenyl]-1,2-benzisothiazole

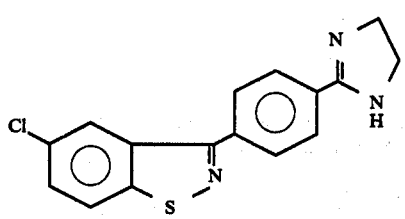

44 g of 5-chloro-3-(4'-chloromethylphenyl)-1,2-benzisothiazole, 9.6 g of sulfur and 18 g of ethylenediamine in 500 ml of toluene are refluxed for 20 hours. The reaction mixture is filtered hot, the filtrate is cooled and the resulting crystals are filtered off. After recrystallization from toluene in the presence of active charcoal, 26 g of 5-chloro-3-[4-(imidazolin-2-yl)-phenyl]-1,2-benzisothiazole, melting at 195° C., are obtained. The yield corresponds to 55% of theory.

| | | C | H | N | S | Cl |
|---|---|---|---|---|---|---|
| Analysis: | calculated | 61.2 | 3.8 | 13.4 | 10.2 | 11.3 |
| | found | 61.0 | 3.9 | 13.3 | 10.3 | 11.4 |

EXAMPLE 5

5-Chloro-3-[4-(methylimidazolin-2-yl)-phenyl]-1,2-benzisothiazole hydrochloride

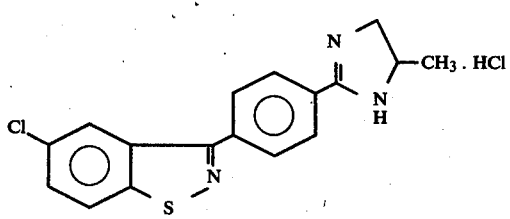

44 g of 5-chloro-3-(4'-chloromethylphenyl)-1,2-benzisothiazole, 9.6 g of sulfur and 22.5 g of 1,2-diaminopropane in 600 ml of toluene are refluxed for 24 hours. The reaction mixture is filtered hot and the filtrate is concentrated on a rotary evaporator. The residue is dissolved in 500 ml of ether and 30 g of hydrogen chloride gas are passed into the solution, whilst cooling. The resulting crystals are filtered off and recrystallized from water. 31 g of product melting, with decomposition, at 248° C., are obtained. The yield corresponds to 57% of theory.

| | | C | H | N | S | Cl |
|---|---|---|---|---|---|---|
| Analysis: | calculated | 56.0 | 4.1 | 11.5 | 8.8 | 19.5 |
| | found | 55.8 | 4.2 | 11.4 | 8.7 | 19.6 |

Formulation Examples prepared in the conventional manner:

1. Tablets:

| a) An active ingredient of the formula I | 5 mg |
|---|---|
| Lactose | 200 mg |
| Methylcellulose | 15 mg |
| Corn starch | 50 mg |
| Talc | 11 mg |
| Magnesium stearate | 4 mg |
| | 285 mg |
| b) An active ingredient of the formula I | 20 mg |
| Lactose | 178 mg |
| Avicel | 80 mg |
| Polywax 6000 | 20 mg |
| Magnesium stearate | 2 mg |
| | 300 mg |
| c) An active ingredient of the formula I | 50 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 280 mg |

The active ingredient is moistened with a 10% strength aqueous solution of polyvinylpyrrolidone, forced through a sieve of 1.0 mm mesh width and dried at 50° C. The resulting granules are mixed with the polyethylene glycol (mean molecular weight 4,000), hydroxypropylmethylcellulose, talc and magnesium stearate and the mixture is pressed to give tablets weighing 280 mg each.

2. Example of dragees:

| An active ingredient of the formula I | 60 mg |
|---|---|
| Lactose | 90 mg |
| Corn starch | 60 mg |
| Polyvinylpyrrolidone | 6 mg |
| Magnesium stearate | 1 mg |
| | 217 mg |

The mixture of the active ingredient with lactose and corn starch is moistened with an 8% strength aqueous solution of polyvinylpyrrolidone, granulated by passing through a 1.5 mm sieve, dried at 50° C. and then forced through a 1.0 mm sieve. The resulting granules are mixed with magnesium stearate and pressed to form dragee cores. The resulting cores are coated in the conventional manner with a covering consisting essentially of sugar and talc.

3. Capsule formulation:

| An active ingredient of the formula I | 5.0 mg |
|---|---|
| Magnesium stearate | 2.0 mg |
| Lactose | 19.3 mg |

4. Injection solution:

| An active ingredient of the formula I | 10 mg |
|---|---|
| Sodium chloride | 9 mg |
| Distilled water, to make up to 1.0 ml. | |

We claim:

1. A compound of the formula I

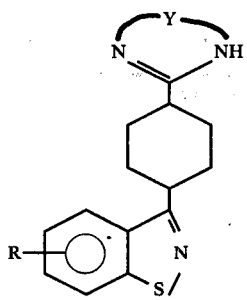 (I)

where R is hydrogen, alkyl of 1 to 4 carbon atoms, alkoxy of 1 to 3 carbon atoms, halogen or nitro and Y is a bridge member of the formula

—$CH_2$—$CH_2$—,

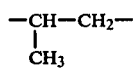

or

—$CH_2$—$CH_2$—$CH_2$, and their physiologically acceptable addition salts with acids.

2. 3-[4-(tetrahydropyrimidin-2-yl)-phenyl]-1,2-benzisothiazole and its physiologically acceptable addition salts with acids.

3. 3-[4-(Methylimidazolin-2-yl)-phenyl]-1,2-benzisothiazole and its physiologically acceptable addition salts with acids.

4. A process for the manufacture of a compound of the formula I, which comprises reacting a compound of the formula II

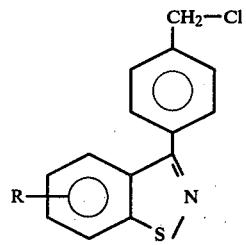 II where R has the meanings given in claim 1, with a diamine of the formula III $H_2N$—Y—$NH_2$ (III)

where Y has the meanings given in claim 1, and with elementary sulfur.

5. A pharmaceutical formulation which comprises a compound of the formula I as the active ingredient, together with conventional pharmaceutical excipients and diluents.

6. A pharmaceutical formulation having an antiarrhythmic effect, which comprises the compound 3-[4-(tetrahydropyrimidin-2-yl)-phenyl]-1,2-benzisothiazole or one of its physiologically acceptable addition salts with an acid, in addition to conventional pharmaceutical excipients and diluents.

7. A pharmaceutical formulation having an antiarrhythmic effect, which comprises the compound 3-[4-(methylimidazolin-2-yl)-phenyl]-1,2-benzisothiazole or one of its physiologically acceptable addition salts with an acid, in addition to conventional pharmaceutical excipients and diluents.

* * * * *